United States Patent [19]

Staba et al.

[11] Patent Number: 4,562,250

[45] Date of Patent: Dec. 31, 1985

[54] STEROIDAL GLYCOSIDES PRODUCED BY YUCCA TISSUE CULTURE

[75] Inventors: E. John Staba; Jean J. MacCarthy, both of Minneapolis, Minn.

[73] Assignee: Regents of the University of Minnesota, Minneapolis, Minn.

[21] Appl. No.: 417,419

[22] Filed: Sep. 13, 1982

[51] Int. Cl.$^4$ .................... C07J 17/00; C07J 19/00
[52] U.S. Cl. .................................. 536/6; 536/6.1; 536/6.3; 260/239.55 A
[58] Field of Search .................... 536/6, 6.1, 6.3

[56] References Cited

U.S. PATENT DOCUMENTS

| | | | |
|---|---|---|---|
| 2,715,122 | 8/1955 | Rothman et al. | 536/6.3 |
| 2,780,620 | 2/1957 | Krider et al. | 536/6.3 |
| 2,785,107 | 3/1957 | Krider et al. | 536/6 |
| 2,895,953 | 7/1959 | Wall et al. | |
| 3,471,470 | 10/1969 | Heider et al. | 536/6 |
| 3,510,400 | 5/1970 | Loken et al. | 260/239.55 A |

FOREIGN PATENT DOCUMENTS

| | | | |
|---|---|---|---|
| 1216009 | of 1966 | Fed. Rep. of Germany | 536/6.1 |
| 48-31917 | of 1973 | Japan | 536/6.1 |

OTHER PUBLICATIONS

Plant Tissue and Cell Culture, Botanical Monographs, vol. 11, H. E. Street (Ed), University of California Press, 1977.
Stohs, Rosenberg and Billets, Planta Medica, 27, 257-261, 1975.
Stohs and Rosenberg, Lloydia, 38(3), 181-194, 1975.
Jhang, Staba and Kim, In Vitro, 9(4), 253-259, 1974.
Marshall and Staba, Phytochemistry, 15, 53-55, 1976.
Tai and Goldberg, Planta Medica, 44, 107-110, 1982.
Tomita et al., Phytochemistry, 9, 111-114, 1970.
Stohs et al., Phytochemistry, 13, 2145-2148, 1974.
Quintero et al., IAPTC Abstr., 1974, Jul. 11-16, 1982, Tokyo.
Jain, Rosenberg and Stohs, Planta Medica, 31, 109-111, 1977.

*Primary Examiner*—Johnnie R. Brown
*Attorney, Agent, or Firm*—Burd, Bartz & Gutenkauf

[57] ABSTRACT

Methods for the production of steroids (sapogenins) and steroidal glycosides (saponins) from cell, root-cell and shoot tissue cultures of the Yucca plant. The cultures were established and maintained in a suitable nutrient plant cell medium supplemented with growth regulators. The desired products are extracted from the cultures using conventional extraction techniques. Greater total production of steroidal glycosides occurred in root-cell, cell, and shoot tissue cultures in that order. Although the cultures may be grown under conditions ranging from total darkness to total light, steroidal glycoside production was highest in root-cell cultures grown continuously in the light as compared to those grown in the dark. Root-cell culture senescence also enhanced the yield of total steroidal glycosides. Steroids are obtained from the steroidal glycosides by acid hydrolysis to remove the sugar moieties. The production of radio-labeled steroids and steroidal glycosides is disclosed.

2 Claims, No Drawings

STEROIDAL GLYCOSIDES PRODUCED BY YUCCA TISSUE CULTURE

BACKGROUND OF THE INVENTION

1. Field of the Invention

This invention is directed to methods for the production of useful steroids and steroidal glycosides, including radio-labeled steroids and steroidal glycosides, by the establishment and maintenance of serially propagated cultures of Yucca plants, i.e., cell, root-cell and shoot cultures, and extraction of steroids and steroidal glycosides from the cultures. The plant tissue cultures are a unique biological source of Yucca steroidal glycosides (saponins).

2. The Prior Art

The initiation, maintenance and uses of various plant tissue culture systems have been well documented (in Plant Tissue and Cell Culture, Botanical Monographs, Volume 11, H.E. Street (Ed), University of California Press, 1977). Stohs, Rosenberg and Billets, Planta Medica 27, 257–261, 1975, have published a comprehensive review of the literature on steroid and sterol metabolism in plant cultures.

Various Yucca plant species produce steroidal saponins (Rothman et al, U.S. Pat. No. 2,715,122; Wall et al, U.S. Pat. No. 2,895,953). Sapogenins have been isolated from various parts of the Yucca plant (Stohs and Rosenberg, Lloydia 38(3), 181–194, 1975). The major steroids of Yucca are sarsasapogenin, its isomer smilagenin, markogenin, tigogenin, hecogenin, markogenin and gitogenin.

The use of diosgenin as a precursor of steroid hormones led to the investigation of plant tissue cultures as a source of steroids. Jhang, Staba and Kim (In Vitro 9(4), 253–259, 1974) established undifferentiated callus and cell suspensions of *Panax quinquefolium* (American Ginseng) and *Panax ginseng* (Korean Ginseng) which produced approximately 4% dry weight of steroidal glycosides. Metz & Lang received German Pat. No. 1,216,009 (1966) and Furuya received Japanese Pat. No. 48-31917 (1973) for Ginseng saponin production by ginseng root or cell cultures. There are several reports on the production of the steroid diosgenin by undifferentiated tissue cultures of Dioscorea species (Marshall and Staba, Phytochemistry 15, 53–55, 1976; Tai and Goldberg, Planta Medica 44, 107–110, 1982; Tomita et al, Phytochemistry 9, 111–114, 1970). Stohs et al (Phytochemistry 13, 2145–2148, 1974) incorporated [4-$^{14}$C-22, 23-$^{3}$H] sitosterol into diosgenin of *Dioscorea deltoidea* cell suspensions. Stohs et al (1974, supra) indicated that undifferentiated callus cultures of *Yucca glauca* grown on solid medium produced the sapogenin gitogenin and trace levels of the sapogenin markogenin. However, when the callus culture was passed into liquid medium and grown as a suspension culture, the ability to biosynthesize steroidal sapogenins was limited (Stohs et al, 1975, supra). Quintero et al (IAPTC Abstr., 1974, July 11–16, 1982, Tokyo) reported *Yucca filifera* callus cells to contain the steroid sarsasapogenin. Jain, Rosenberg and Stohs (Planta Med. 31: 109–111, 1977) isolated the sapogenins tigogenin and gitogenin from callus cultures of *Trigonella foenium-graecum*.

To date, the production of Yucca steroidal glycosides from Yucca tissue cultures has not been reported.

SUMMARY OF THE INVENTION

Broadly stated, the invention is directed to methods for the production of Yucca steroidal glycosides from Yucca tissue cultures.

A tissue culture of Yucca plant is first established on a nutrient plant cell medium containing a growth regulator. This culture which may be cell, root-cell or shoot tissue, is maintained under growth conditions until callus is produced. The culture is subcultured by transfer to a liquid nutrient plant cell medium containing a growth regulator. The liquid subculture is maintained under growth conditions until optimum culture growth and steroidal glycoside production has been achieved, usually about four to six weeks after subculturing. The Yucca plant tissue cultures are then harvested from the medium and the steroidal glycosides are extracted. Although culture growth occurs under conditions ranging from total darkness to total light, preferably the cultures are grown in light since greater steroidal glycoside production results. Steroids are obtained from the steroidal glycosides by acid hydrolysis to remove the sugar portion of the molecule. By incorporating a radio-labeled precursor in the initial tissue culture, radio-labeled steroidal glycosides and steroids are produced.

DETAILED DESCRIPTION OF THE PREFERRED EMBODIMENT

Steroidal glycosides (saponins) consist of a steroid (sapogenin) and a sugar. Saponins from Yucca plants, now added as parts of Yucca plants, are used as animal feed additives. Yucca plants grow in desert and semi-arid areas, for example, in the American Southwest and Mexico. They are subject to seasonal variations in crop size and availability. The strong fibrous shoots present special problems for mechanical harvesters. Because of this, the shoots are often harvested manually. Fibrous Yucca plant tissues are not readily extractible and require special presses or mills.

By contrast, tissue suspension cultures of Yucca are readily established and are a manageable biological source of Yucca steroidal glycosides. The cultures can be maintained continuously and under well defined cultural conditions. The steroidal glycosides are easily harvested and extracted. Yucca cell and organ cultures grow rapidly. Steroidal glycoside production by Yucca tissue cultures can be enhanced and controlled by manipulating culture conditions. Furthermore, the tissue cultures are easily incubated with radio-labeled substrates to biosynthesize radio-labeled saponins, not presently commercially available for biochemical and other applications.

Although the invention is described with particular reference to *Yucca schidigera*, the invention is applicable to all species of Yucca plant. Exemplary among these are *Y. peninsularis, Y. whipplei, Y. angustissima, Y. arizonica, Y. baccata, Y. elata, Y. faxoniana, Y. brevifolia, Y. mohavensis, Y. filifera*, etc. Specific steroidal saponin content varies with plant species.

The culture is initiated by selecting appropriate Yucca tissue and growing on a nutrient plant cell medium containing a growth regulator. To insure sterile conditions, the culture is preferably initiated with seedling tissue produced from aseptically germinated seeds. If non-aseptic plant portions are used, they are sterilized before introduction to the medium.

Although others may be used, a preferrred medium is Murashige and Skoog's revised tobacco medium (MS)

containing agar. This solid medium preferably contains a growth regulator such as 2,4-dichlorophenoxyacetic acid (2,4-D), a cytokinin-like growth regulator such as kinetin and/or benzyladenine, and auxin-like growth regulator such as naphthaleneacetic acid (NAA) or indoleacetic acid, or the like, depending upon the particular plant portion desired to be produced. For example, 2,4-D promotes cell growth. Cytokinin-like regulators promote shoot growth, and auxin-like regulators promote root growth.

When 2,4-D is used, it is incorporated into the medium in amount between about 0.001 to 10 ppm, and preferably 0.01 to 1 ppm. When benzyladenine is used, it is incorporated into the medium in amount between about 0.001 to 30 ppm, and preferably about 0.01 to 5 ppm. If kinetin is used, the amounts range from about 0.001 to 40 ppm, and preferably about 0.01 to 6 ppm; naphthaleneacetic acid about 0.001 to 15 ppm, and preferably about 0.5 to 5 ppm, and indoleacetic acid about 0.01 to 10 ppm, and preferably about 0.5 to 5 ppm.

The initial culture is maintained under aerobic culture growth conditions at a temperature of about 10° to 38° C. for a period of 1 to 12 weeks until callus is produced. The initial incubation preferably takes place in the dark.

The cultures are then subcultured by transfer into a liquid medium, preferably Murashige and Skoog's medium without agar, containing a growth regulator. The amounts are generally within the ranges previously set forth. The liquid cultures are exposed to air and preferably shaken or otherwise gently moved to introduce air to the medium, or air may be introduced through tubing into the culture vessels. The cultures are maintained under appropriate growth conditions at a temperature between about 10° to 38° C. and preferably between about 20° and 30° C. The pH may be from about 3.0 to 8.0 and preferably about 5.0 to 7.0. The culture may be grown under light conditions ranging from total darkness to total light for various periods of time. Because total steroidal glycoside production was highest in cultures grown continuously in the light, this is preferred. Typical light conditions range between about 100 to 3000 foot candle power.

The cultures are maintained for up to about six to seven weeks from the time of subculturing, after which culture growth declines. The cultures are harvested by removal of the growth medium, as by filtration. The harvested culture is dried, as by lyophylization, ground to a fine powder, and the steroidal glycosides are extracted by use of conventional solvent extraction techniques. The corresponding steroids are obtained from the steroidal glycosides by conventional acid hydrolysis to remove the sugar portion of the molecule.

The cultures grown in light became green quite readily. This greening did not take place when the cultures were placed in the dark immediately following subculture. The cultures developed a brown color in the light with approaching senescence as active growth ceased and a stationary phase in the growth cycle was entered, after about six to seven weeks from subculturing. However, there is an apparent increased accumulation of steroidal glycosides in tissues undergoing senescence. In order, the greater production of total steroidal glycosides occurred in root-cell, cell, and shoot tissue cultures.

Radio-labeled steroidal glycosides and steroids are produced by incubating tissue cultures with a radiolabeled precursor such as [1-$^{14}$C] acetate. The cultures are incubated under the suspension subculture conditions already described. The time of incubation may range between about 2 to 25 hours. At the end of the incubation, the culture is washed to remove residual radio-acid isotope and then the tissue is harvested and the radio-labeled steroidal glycoside separated in the same manner already described. The radio-labeled steroids are obtained by acid hydrolysis of the steroidal glycosides.

The invention is illustrated by the following examples:

EXAMPLE 1

Seeds of *Yucca schidigera* (family Liliaceae) were germinated aseptically to produce seedling tissue. This seedling tissue was placed on revised Murashige and Skoog (MS) medium containing 1.0 ppm 2,4-D and incubated in the dark until callus was produced.

The callus was subcultured into liquid revised MS medium supplemented with 3.0 ppm naphthaleneacetic acid (NAA). It was then incubated on a shaker rotating at 78 rpm, at 25°±2° C. and in the light. The light cycle was 16 hours light, 8 hours darkness. Illumination was provided by General Electric fluorescent white lights and Westinghouse incandescent lights. The light intensity was 500 foot-candles.

With time, root-like tissues developed from the callus in liquid medium. These root-cell cultures became green quite readily and this greening did not occur if the cultures were placed in the dark immediately following subculture. Cultures eventually developed a brown color in the light. This occurred when the culture ceased active growth and had entered stationary phase in the growth cycle. Cells of the green pigmented cultures had large, well defined chloroplastids. The culture consisted of root-like tissues and cells (single or as small aggregates). The roots were initially triangle shaped, but subsequently developed well defined branches or arms (2–3). These branches had protuberances which could correspond to rudimentary root hairs or branches of a diffuse root system. The root tissues actually developed root hairs when placed on solid (agar supplemented) modified MS medium with 3 ppm NAA in the dark. When examined in the light microscope, these root tissues had typical anatomical features of a root: cap-like root tip, zone of small (possibly dividing) cells, and a zone of elongated cells.

Growth of root-cell culture increased up to about six weeks from time of subculture, and then declined.

Green pigmented (0.37 grm dry weight) and brown pigmented (0.22 grm dry weight) root-cell cultures were harvested for extraction and analysis. Growth medium was removed by suction filtration. Harvested culture was lyophylized until dry, ground to a fine powder and placed in a single thickness cellulose extraction thimble (Whatman). The thimble was plugged with glass wool to prevent loss of the powder during extraction and then placed in a glass Soxhlet apparatus.

Tissues were defatted twice using chloroform. Each defatting period ran for 8 hours and approximately 100 ml chloroform was used each time. The yield was 21.1 mg lipid per gram dry weight for green pigmented tissues, and 19.4 lipid per gram dry weight for brown pigmented tissues. Placing green root-cell tissues in the dark for one week prior to harvest raised the lipid yield to 33.8 mg per gram dry weight.

Following lipid removal, tissues and Soxhlet thimbles were air-dried, and then extracted twice for steroidal glycosides using n-butanol as the extracting solvent. Each extraction was done for 8 hours and used approximately 100 ml n-butanol. The n-butanol fractions were pooled, and n-butanol removed using a Buchler flash evaporator. The dried extract was weighed and redissolved in n-butanol for analysis. The total steroidal glycoside yield was as follows: 213.1 mg per gram dry weight for green pigmented tissues: 370.3 mg per gram dry weight for brown pigmented tissues. This indicated that there may be increased accumulation of steroidal glycosides in tissue undergoing senescence. The total saponin yield for green pigmented tissues placed in the dark one week before harvesting was 151.9 mg/gram dry weight indicating that optimal saponin synthesis occurred in the light.

The n-butanol extracts were analyzed for individual steroidal glycosides using thin-layer chromatography (TLC). Glass plates precoated with 250 microns silica gel G (Analtech) were used. The solvent system was chloroform:methanol:water, 65:25:1 (v/v/v). The tissue culture extracts were co-chromatographed with an extract of Y. schidigera plant from Distributors Processing, Inc., Porterville, Calif. Steroidal glycosides of this plant extract had previously been identified by cleaving the steroids from the sugars then identifying the steroids. This was done by the acid hydrolysis method described below. Steroidal glycosides were visualized by spraying the TLC plate with ceric sulfate spray reagent (3% ceric sulfate in 50% sulfuric acid, w/v). The plate was then heated at 120° C. for 5 minutes.

Based on this comparison, steroidal glycosides containing the steroids tigogenin ($5\alpha, 20\alpha, 22\alpha, 25D$-spirostan-$3\beta$-ol), hecogenin ($5\alpha, 20\alpha, 22\alpha, 25D$-spirostan-$3\beta$-ol-12-one) sarsasapogenin ($5\beta, 20\alpha, 22\alpha, 25S$-spirostan-$3\beta$-ol), and 11, ketotigogenin ($5\alpha, 20\alpha, 22\alpha, 25D$-spirostan-$3\beta$-ol-11-one) were identified as having been present in the brown pigmented tissues. Steroidal glycosides containing the steroids tigogenin, hecogenin, sarsasapogenin, 11, ketotigogenin and markogenin were identified as having been present in the green pigmented tissues.

The unhydrolyzed n-butanol extract was further fractionated using gravity column chromatography. This technique gave steroidal glycoside fractions sufficiently purified for Nuclear Magnetic Resonance (NMR) Spectrometer analysis. This permitted a determination of the true steroidal glycoside nature of the metabolites produced by the Yucca root cell cultures. A steroid linked to one or more sugar moieties gives a characteristic NMR spectrum profile. A glass column (Altek; 1.0 cm×500 cm) was packed with the adsorbent silica gel 60 (Merck; particle size 0.040–0.063 mm). The n-butanol was removed from the tissue culture extract by evaporation under nitrogen. The extract was redissolved in methanol and an aliquot equivalent to 45.4 mg was applied to the gravity column. The eluting solvent was methanol-chloroform. The polarity of the eluting solvent was increased from 5% methanol in 95% chloroform by increments of 5% for every 20 column fractions, to 40% methanol in 60% chloroform. The 2 ml fractions were collected using a Model 328 ISCO Retriever 111 fraction collector. Column fractions were evaporated to dryness under nitrogen, redissolved in methanol-chloroform and screened for steroidal glycosides using TLC as described above. Fractions having identical TLC Rf values were pooled for subsequent NMR analysis. A JEOL FX 90 Q Fourier Transform NMR spectrometer (60 MHz) was used. Spectra characteristic of a steroid molecule linked to one or more sugar molecules were obtained. One of these pooled gravity column fractions corresponded to the steroidal glycoside containing sarsasapogenin and tigogenin as steroids.

EXAMPLE 2

To establish that Yucca root cell cultures were capable of de novo steroidal glycoside synthesis, and to produce radio-labeled steroidal glycosides and steroids, incubations were done with the radio-labeled precursor [$1$-$^{14}C$] acetate. Green Yucca root culture was grown 7 weeks from subculture. Culture (0.5 grm fresh weight) was incubated with 17.85 nmoles of [$1$-$^{14}C$] acetate, sodium salt (New England Nuclear; specific activity 56 mCi.mmol$^{-1}$) in 1.5 ml of sterile modified MS medium (supplemented with 3.0 ppm NAA). Cultures were incubated on a shaker rotating at 78 rpm and at a temperature of $25\pm2°$ C. Incubations were made in the light and in the dark, at incubation medium pH 6.0 and at incubation medium pH 7.0. The photoperiod in the light was 8 hours 20 minutes. Time of incubation was either 16 hours 20 minutes, or 5 hours 50 minutes (in the light). At the end of the incubation, culture was washed once to remove residual radioisotope, harvested by suction filtration and lyophilized. Lyophylized tissue was extracted and analyzed by TLC for [$^{14}C$] steroidal glycosides, as described in Example 1.

An aliquot (100 $\mu$l) of the n-butanol extract was dissolved in 10 ml of the liquid scintillant Phase Combining System (PCS; Amersham Corp.) in counting vials and counted for incorporation of [$^{14}C$] label into total [$^{14}C$] steroidal glycosides using a Beckman LS 100C scintillation counter. The percent incorporation of [$1$-$^{14}C$] acetate into total [$^{14}C$] steroidal glycosides following incubation for 16 hours 20 minutes was as follows: 11.6% (pH 6.0; in the light); 15.4% (pH 7.0: in the light); 8.4% (pH 6.0; in the dark). Incorporation was 5.9% following an incubation of 5 hours 50 minutes in the light and at pH 6.0. This indicated that optimal synthesis of Yucca [$^{14}C$] steroidal glycosides occurred in the light and at a medium pH 7.0. Synthesis of total [$^{14}C$] steroidal glycosides increased as the culture entered stationary phase of growth.

The n-butanol extracts were analyzed for individual [$^{14}C$] steroidal glycosides using analytical TLC as described above. Individual [$^{14}C$] steroidal glycosides were also isolated using preparative TLC. Glass preparative plates precoated with 100 microns silica gel G were used. The solvent system for both analytical and preparative TLC was chloroform:methanol:water, 65:25:1 (v/v/v). Analytical and preparative plates were scanned using a Berthold Radiochromatogram plate scanner. [$^{14}C$] Steroidal glycosides were located using the scan chromatogram. Individual [$^{14}C$] steroidal glycoside bands were marked on preparative plates. Each marked band was scraped and eluted 3 times with methanol:chloroform (65:1, v/v).

The eluted [$^{14}C$] steroidal glycosides were hydrolyzed with methanolic 6N HCl at 90° C. for 14 hours. Residual silica gel of the scraped TLC bands was also treated directly with methanolic 6N HCl at 90° C. for 14 hours to hydrolyze any [$^{14}C$] steroidal glycoside still adhering to the silica gel. The hydrolysate was cooled and the [$^{14}C$] steroids were extracted from the aqueous phase with chloroform.

[$^{14}C$] Steroids recovered from the hydrolysate were co-chromatographed with authentic steroid reference compounds using analytical TLC as described in Example 1. Plates were scanned with a Berthold Radiochromatogram TLC plate scanner to localize [$^{14}$C] steroids. Reference steroids were localized using ceric sulfate spray reagent. [$^{14}$C] Steroids were thus identified by comparison of TLC characteristics with reference compounds.

By this technique, saponins, such as those containing [$^{14}$C] hecogenin, [$^{14}$C] markogenin and [$^{14}$C] 11, ketotigogenin were identified as metabolites synthesized by Yucca root cultures under the conditions described.

By the extraction and analysis techniques described, cells grown on MS medium supplemented with 1 ppm 2,4-D contained glycosides resulting in 130 mg total steroids/grm dry wt, and shoots grown on MS medium supplemented with 3.0 ppm benzyladenine (BA) contained glycosides resulting in 200 mg total steroids/grm dry wt. Shoot cultures contained markogenin, hecogenin and 11, ketotigogenin.

There has been described a process for establishing tissue cultures of the American desert plant *Yucca schidigera*. This is the first time that a procedure for establishing root cell suspension cultures of *Y. schidigera* has been described. This culture and cell and shoot cultures produced steroidal glycosides containing Yucca steroids. Conditions (light and senescence) affecting optimal steroidal glycoside production have been disclosed. Production of [$^{14}$C] steroidal glycosides has been disclosed, as well as conditions (light, pH, length of incubation with [$^{14}$C] substrate) for optimal production.

It is apparent that many modifications and variations of this invention as hereinbefore set forth may be made without departing from the spirit and scope thereof. The specific embodiments described are given by way of example only and the invention is limited only by the terms of the appended claims.

I claim:

1. Radio-labeled steroidal glycosides of the Yucca plant produced by:
    (A) establishing a tissue culture of Yucca plant on a nutrient plant cell medium containing a growth regulator,
    (B) maintaining under growth conditions,
    (C) transferring the resulting culture to a liquid nutrient plant cell medium containing a growth regulator,
    (D) maintaining the liquid and subculture under growth conditions,
    (E) incubating the liquid subculture toward the end of its growth cycle with a radioactive isotope, and
    (F) harvesting the Yucca plant tissue cultures from the medium and extracting the resulting radio-labeled steroidal glycosides therefrom.

2. Radio-labeled steroidal glycosides according to claim 1 wherein the glycosides are [$^{14}$C] steroidal glycosides.

* * * * *